United States Patent
Yang et al.

(10) Patent No.: US 8,180,140 B2
(45) Date of Patent: May 15, 2012

(54) TEMPLATE CREATION METHOD AND IMAGE PROCESSOR THEREFOR

(75) Inventors: Kyoungmo Yang, Mito (JP); Makoto Nishihara, Hitachinaka (JP); Shunsuke Koshihara, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 693 days.

(21) Appl. No.: 12/399,367

(22) Filed: Mar. 6, 2009

(65) Prior Publication Data

US 2009/0304286 A1 Dec. 10, 2009

(30) Foreign Application Priority Data

Mar. 7, 2008 (JP) ................................. 2008-057157

(51) Int. Cl.
*G06K 9/00* (2006.01)
(52) U.S. Cl. ...................................... 382/144; 382/209
(58) Field of Classification Search .................... 382/144
See application file for complete search history.

(56) References Cited

U.S. PATENT DOCUMENTS

| | | | |
|---|---|---|---|
| 4,659,179 A * | 4/1987 | Dominique et al. | 359/396 |
| 6,678,414 B1 * | 1/2004 | Loce et al. | 382/209 |
| 7,026,615 B2 * | 4/2006 | Takane et al. | 250/310 |
| 7,178,114 B2 * | 2/2007 | Lin et al. | 716/122 |
| 7,235,782 B2 * | 6/2007 | Takane et al. | 250/310 |
| 7,365,322 B2 * | 4/2008 | Miyamoto et al. | 250/310 |
| 7,836,398 B2 * | 11/2010 | Hirai | 715/243 |
| 7,923,703 B2 * | 4/2011 | Morokuma et al. | 250/492.22 |
| 2002/0118893 A1 * | 8/2002 | Nguyen et al. | 382/294 |
| 2002/0158199 A1 * | 10/2002 | Takane et al. | 250/310 |
| 2003/0173516 A1 * | 9/2003 | Takane et al. | 250/310 |
| 2004/0081350 A1 * | 4/2004 | Kitamura et al. | 382/149 |
| 2004/0225986 A1 * | 11/2004 | Lin et al. | 716/10 |
| 2006/0126916 A1 * | 6/2006 | Kokumai | 382/151 |
| 2006/0193508 A1 * | 8/2006 | Sutani et al. | 382/145 |
| 2006/0284081 A1 * | 12/2006 | Miyamoto et al. | 250/307 |
| 2007/0187599 A1 * | 8/2007 | Abe et al. | 250/310 |
| 2008/0250380 A1 * | 10/2008 | Kijima et al. | 716/18 |

FOREIGN PATENT DOCUMENTS

JP 2002-328015 11/2002

* cited by examiner

*Primary Examiner* — Sath V Perungavoor
(74) *Attorney, Agent, or Firm* — McDermott Will & Emery LLP

(57) ABSTRACT

To create a template for use in image recognition based on design data, luminance information is set for each area in the template based on the information regarding the region defined by the template. The luminance information may be set based on material information, pattern size information of a pattern arranged in the region defined by the template, and layer information of the region defined by the template. Alternatively, luminance information may be set based on material information, setup conditions of the scanning electron microscope, and pattern outline information of a pattern arranged in the region defined by the template.

4 Claims, 16 Drawing Sheets

$OUT_{METAL} > OUT_{QUARTZ}$ $OUT_{FILM\,1} > OUT_{FILM\,2}$ $OUT_{PATTERN1} < OUT_{PATTERN2}$ (a)

| Material | E2(Kev) | Reference |
|---|---|---|
| Electron resist | 0.55~0.70 | Joy(1987) |
| Glass passivation | 2.0 | Joy(1987) |
| GaAs | 2.6 | Joy(1987) |
| Quartz | 3.0 | Joy(1987) |
| Alumina | 4.2 | Joy(1988) |

(b)

(c)

TEMPLATE CREATION METHOD AND IMAGE PROCESSOR THEREFOR

BACKGROUND OF THE INVENTION

1. Field of the Invention

The present invention relates to a method for creating templates that are used to detect a particular position in a semiconductor device and to an image processor and a program therefore and, in particular, to a template creation method based on the design data of a semiconductor device or the like.

2. Description of the Related Art

Conventional semiconductor measurement devices recognize an image by comparison between SEM (scanning electron microscope) images, between an SEM image and an OM (optical microscope) image, or between OM images. In contrast, some of recent image recognition technologies utilize design data to recognize an image as in comparison between design data and an SEM image or between design data and an OM image.

For example, Japanese Unexamined Patent Application Publication No. 2002-328015 (Patent Document 1, corresponding to U.S. Pat. No. 7,026,615) discloses a technique for creating based on design data (CAD data) a template image to be used for pattern matching in a SEM image. This technique is designed to smooth the design data so as to create a template close to an actual image.

SUMMARY OF THE INVENTION

In image recognition involving comparison between the two images of the same type, the success rate of image recognition can be increased with the use of pattern edge information and contrast information. In image recognition with the use of design data, however, the pattern edge information can be utilized, but the contrast information cannot. Thus, a problem with the latter image recognition is that the success rate of image recognition and its performance cannot be improved beyond a certain level, in comparison with the former image recognition involving comparison between the two images of the same type (e.g., between SEM images or between OM images).

The technique disclosed in Patent Document 1 is designed to supplement the shapes of pattern edge portions in design data so as to reduce the difference in pattern edge shape between the design data and an SEM image, whereby the matching rate between the two can be increased drastically. However, Patent Document 1 is not designed to use the contrast information, which is not present in design data, so as to increase its image recognition performance up to the level of the image recognition that involves same-type image comparison.

An object of the present invention is thus to maintain the ease with which a template is created based on design data without acquiring an actual image, which is achieved by providing the template with equivalent information contained by a template used for image recognition that involves same-type image comparison, and to improve image recognition performance by increasing the matching rate between a template and an actual image.

To achieve the above object, the present invention provides a method, apparatus, and program for creating based on design data a template that is used for image recognition, wherein luminance information is set for each area in the template based on the material information of the region defined by the template. Specifically, the luminance information is set based on at least one of information from among the above material information, the pattern size information of a pattern arranged in the region defined by the template, the setup conditions of an imaging apparatus, the layer information of the region defined by the template, and the outline information of a pattern.

The above configuration can improve image recognition performance using on a template that is created based on design data.

BRIEF DESCRIPTION OF THE DRAWINGS

Other objects and advantages of the invention will become apparent from the following description of embodiments with reference to the accompanying drawings in which.

DETAILED DESCRIPTION OF THE PREFERRED EMBODIMENTS

Described hereinafter with reference to the accompanying drawings is a template creation method with the use of design data, an embodiment of the invention.

Figure 1:
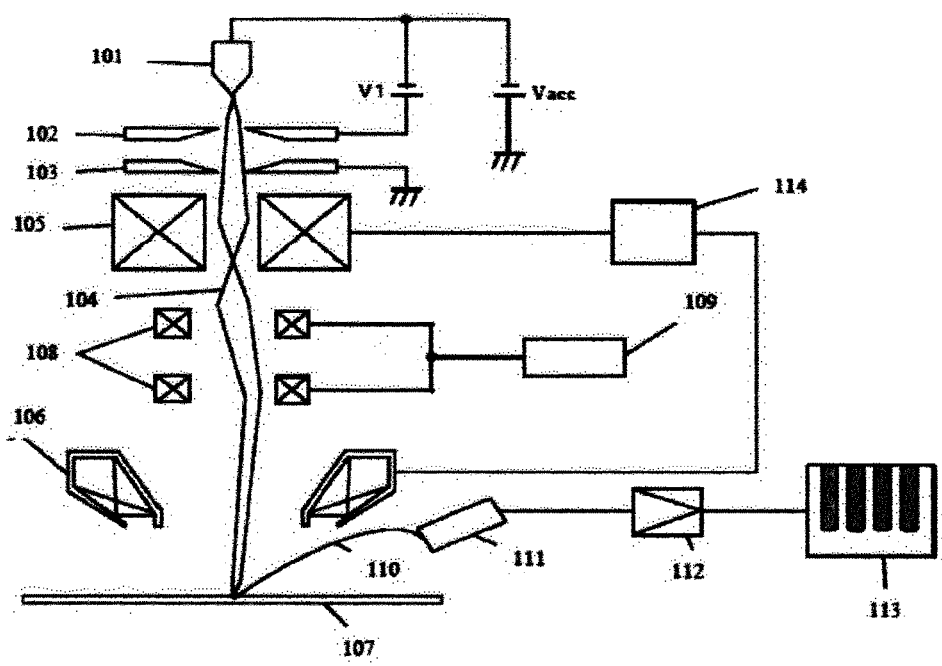
FIG. 1 is a schematic diagram of a scanning electron microscope.

FIG. 1 shows one of the exemplary configurations of an SEM. In the SEM, a primary electron beam 104 is applied to a cathode 101 and a first anode 102 and accelerated toward the subsequent-stage lens system by a voltage Vacc (acceleration voltage) applied to a second anode 103.

The primary electron beam 104 is focused as a tiny spot onto a sample (synonymous with "wafer" or "semiconductor device") 107 by a convergent lens 105 and an objective lens 106, both controlled by a lens control power supply 114. The focused primary electron beam 104 is then two-dimensionally scanned across the sample 107 by two-stage deflecting coils 108. Scanning signals for the deflecting coils 108 are controlled by a deflection control device 109 based on desired image magnifications. By the primary electron beam 104 being scanned across the sample 107, secondary electrons 110 are generated from the sample 107. These secondary electrons 110 are detected by a secondary electron detector 111. The secondary electron information obtained by the secondary electron detector 111 is then amplified by an amplifier 112 and displayed on a CRT 113. In the apparatus shown in FIG. 1, the sample pattern information thus displayed on the CRT 113 is used to automatically measure patterns on the sample 107.

Figure 2:
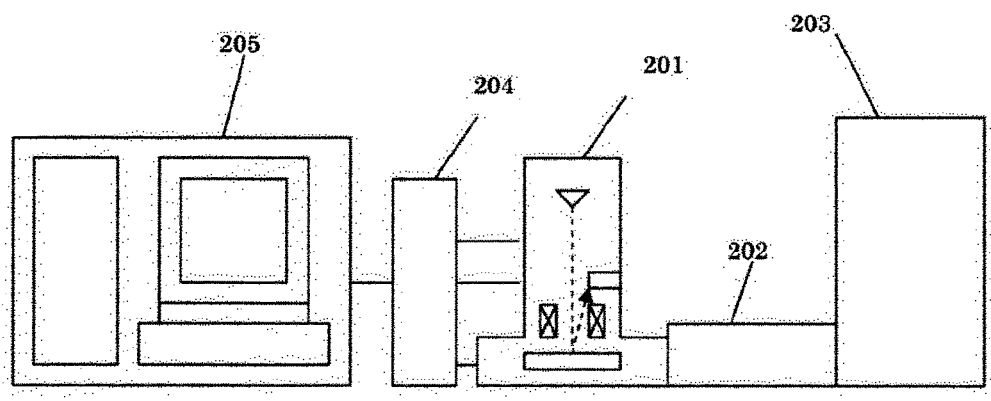
FIG. 2 is a schematic configuration diagram of a system including the SEM.

FIG. 2 illustrates the configuration of a system that incorporates the SEM of FIG. 1. The SEM, designated 201 in FIG. 2, connects to a load lock chamber 202, a mini environment 203, a control device 204, and a design data management device 205. The load lock chamber 202 has a vacuum pump connected thereto so that the pump preliminarily evacuates the vacuum chamber of the SEM upon sample loading. Inside the mini environment 203 is an optical microscope, and images obtained with this optical microscope are used to perform sample pre-alignment. The sample pre-alignment is finely adjusted by an adjusting mechanism (not shown) based on image recognition of the optical microscope so that the sample is positioned at a particular position. The control device 204 is to control the optical elements of the SEM 201, the preliminary evacuation of the SEM vacuum chamber performed in the load lock chamber 202, the optical microscope inside the mini environment 203, and the like. The design data management device 205, part of the image processor according to the invention, stores on its storage medium (not shown) design data of samples to be measured or observed by the SEM. This storage medium also stores a program necessary for creating, based on the design data, templates to be used for pattern matching. As described above, the system of FIG. 2 includes two imaging apparatuses: the SEM 201 and the optical microscope.

Described next is an exemplary program algorithm for template creation by the design data management device 205, which is connected to the above two imaging apparatuses. Although, in FIG. 2, the SEM 201, the control device 204 that controls the SEM 201, and the design data management device 205 are structurally different, it should be noted that the present invention is not limited to that configuration. For example, the control device 204, instead of the design data management device 205, may execute the template creation program by its operational functions.

FIG. 3 are examples of design data of a certain position in a semiconductor device. FIGS. 3A to 3C show the vertically same sample region with respect to the surface of the sample and each show design data of different layers of the sample. FIG. 3A is data of the uppermost layer obtained at the time of SEM measurement, FIG. 3B data of a layer below it. FIG. 3C is design data of a dummy layer, FIG. 3D design data obtained by overlapping the above three layers of design data.

Unlike design data, OM images (those obtained by an optical microscope) include underlayer information and contrast information, which is not represented by design data. When a template is to be created based on design data, appropriately capturing such information enables creation of a template close to an OM image. As a result, the matching rate between the two can be improved drastically. In the present embodiment, the template luminance level is set according to the layers or element materials of a semiconductor device, thereby creating a template close to an actual image.

Specifically, the luminance levels for various positions in a template are determined based on the following rules. 1) Because reflectance differs among positions in a semiconductor device, for example, between an upper layer and a lower layer, the template luminance level is set high for high reflectance positions and low for relatively low reflectance positions. 2) Because reflectance also differs among materials of a semiconductor device, the template luminance level is set according to the reflectance levels of the materials. Below is an example of this template luminance level setting.

Figure 3A:
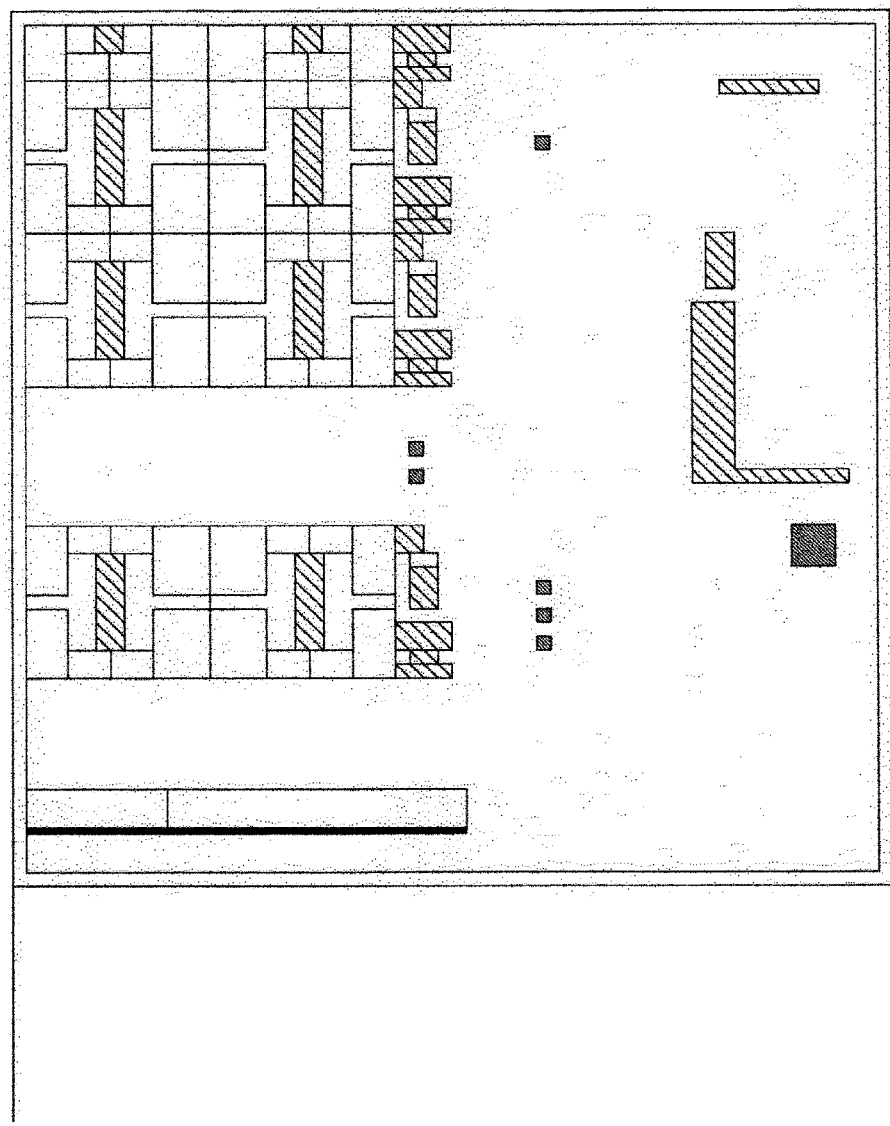
FIGS. 3A to 3D show design data for each layer of a wafer.
Figure 3B:
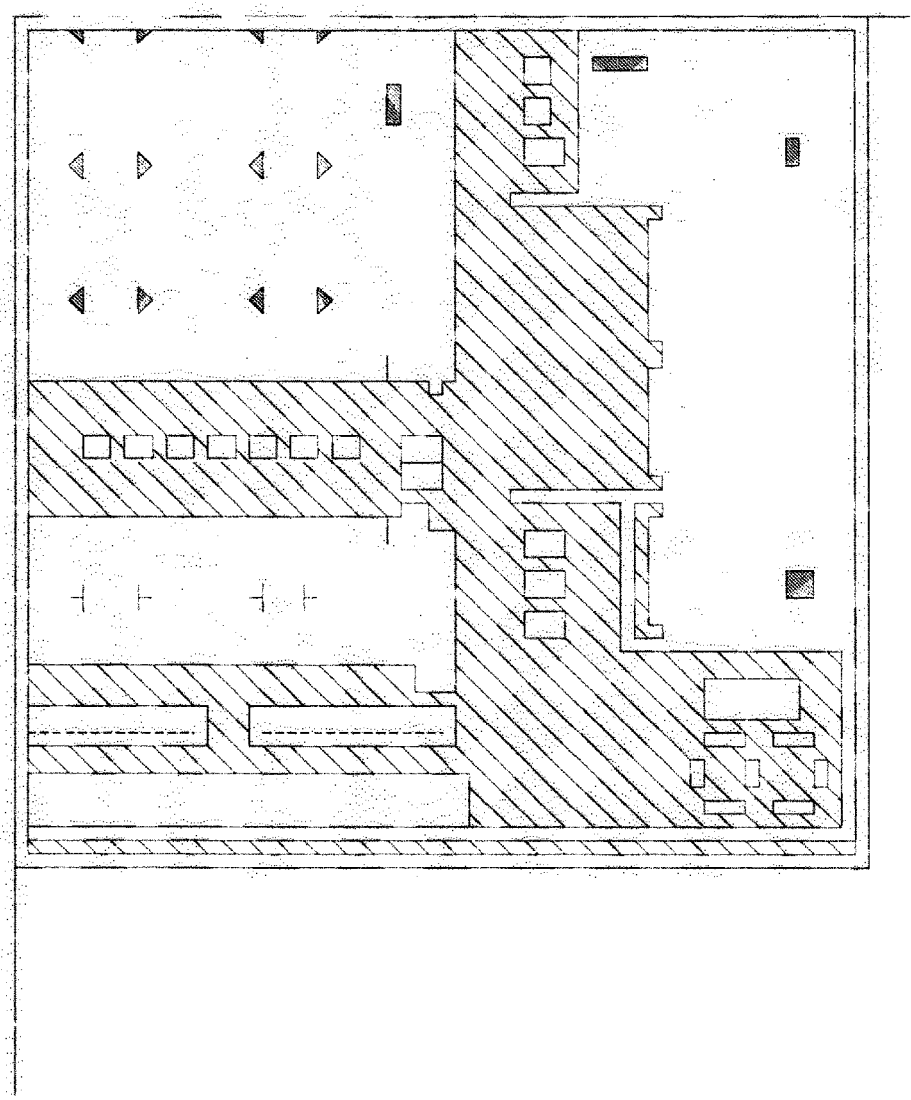
Figure 3C:
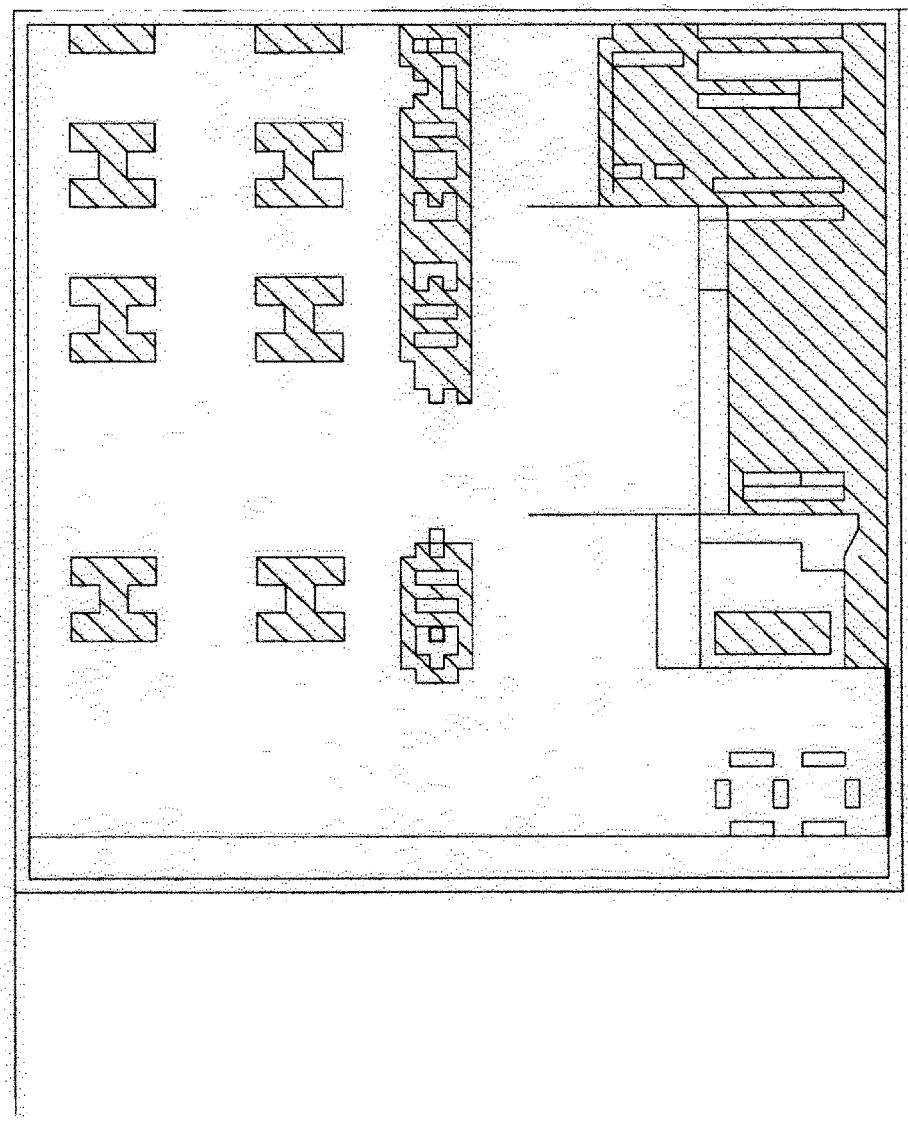
Figure 3D:
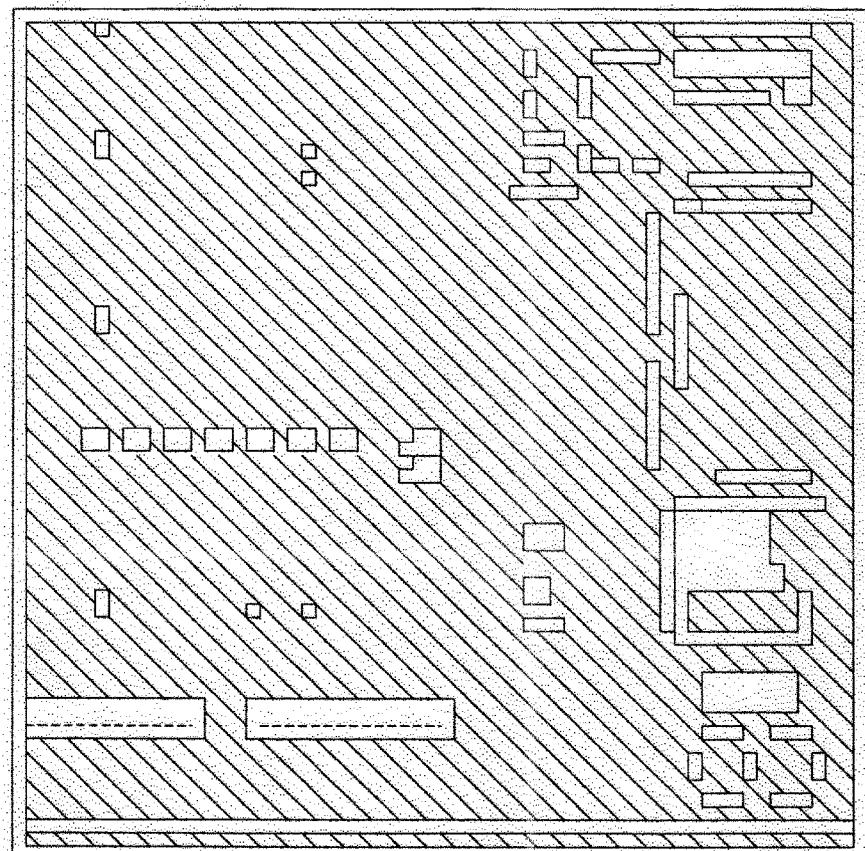
Figure 4A:
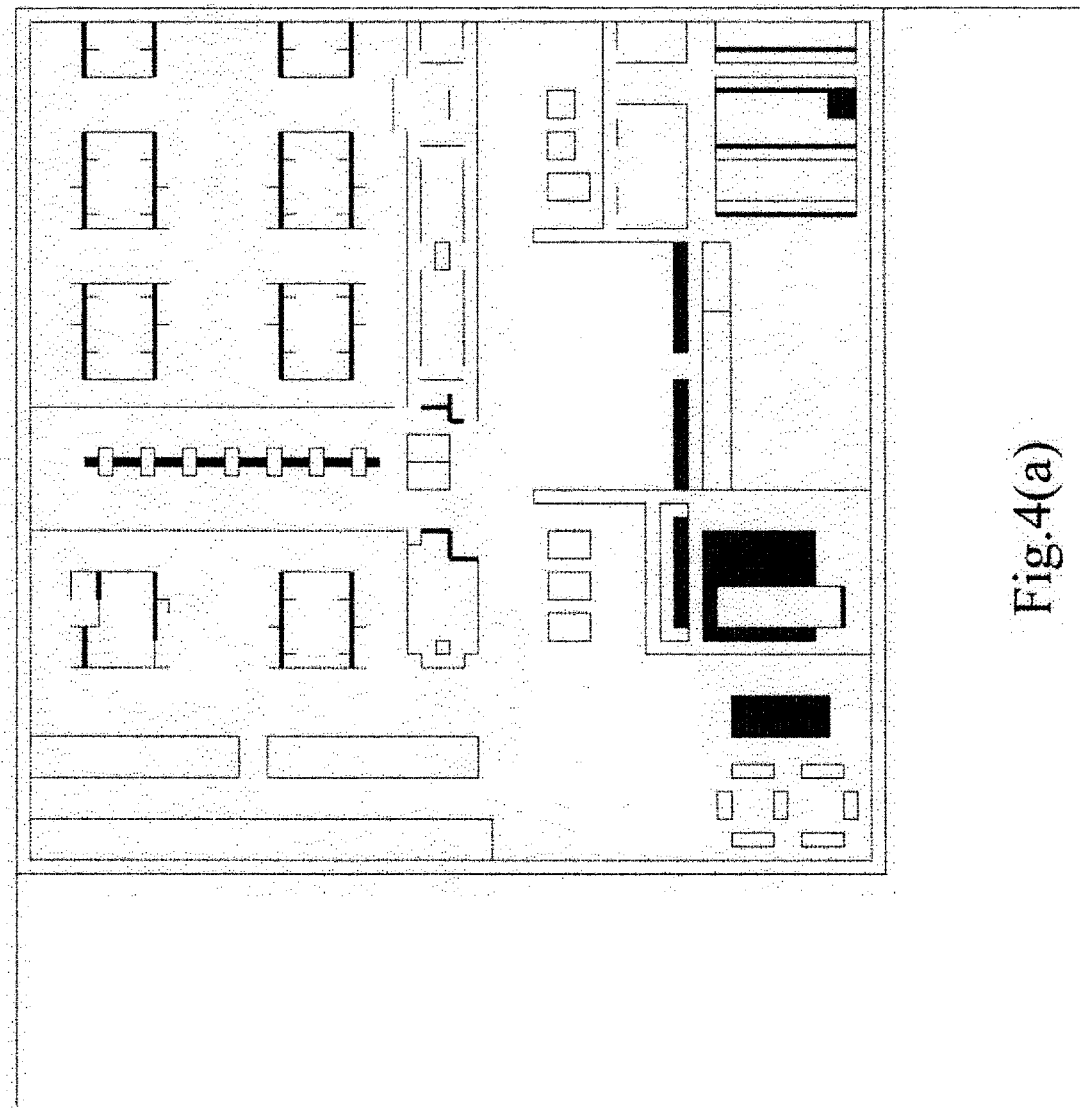
FIG. 4A shows a template used for image recognition when design data for each layer is simply overlapped, FIG. 4B showing its corresponding OM image.
Figure 4B:
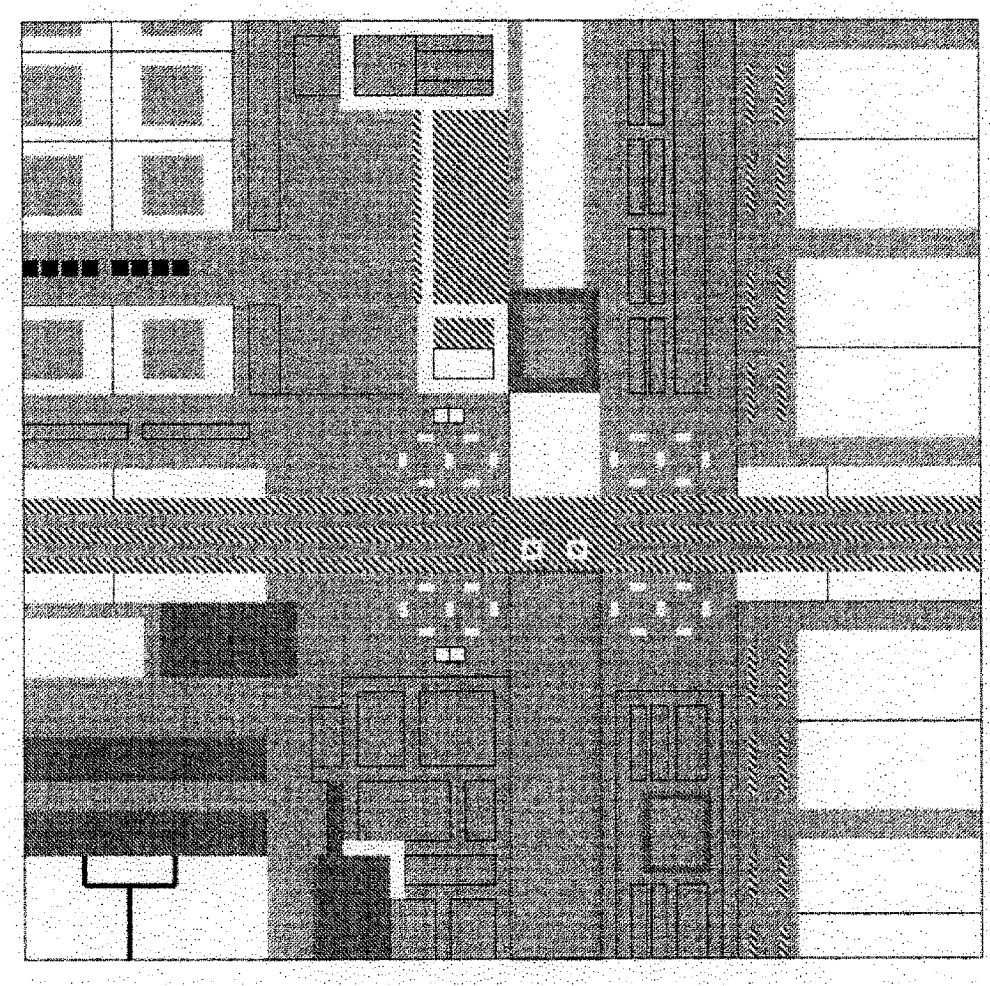

FIG. 4A is an image recognition template based on the design data of FIG. 3D, and FIG. 4B is its corresponding OM image. Note that if the design data of FIG. 3A to 3C are used to create their corresponding image recognition templates, the probability of image recognition failure increases due to a great information amount difference between the design data of FIG. 3A to 3C and the actual OM image of FIG. 4B. For this reason, the composite data of FIG. 3D is used to create a template.

Since design data does not have such contrast information as included by an OM image, it expresses contrast by image binarization (by distinguishing between regions with signals and regions without signals). This results in such an image recognition template in black and white as shown in FIG. 4A. As can be seen, there is a significant information difference between the template of FIG. 4A, in which different layers of the semiconductor device are indistinguishable, and the actual OM image of FIG. 4B, suggesting a high probability of image recognition failure.

Figure 5A:
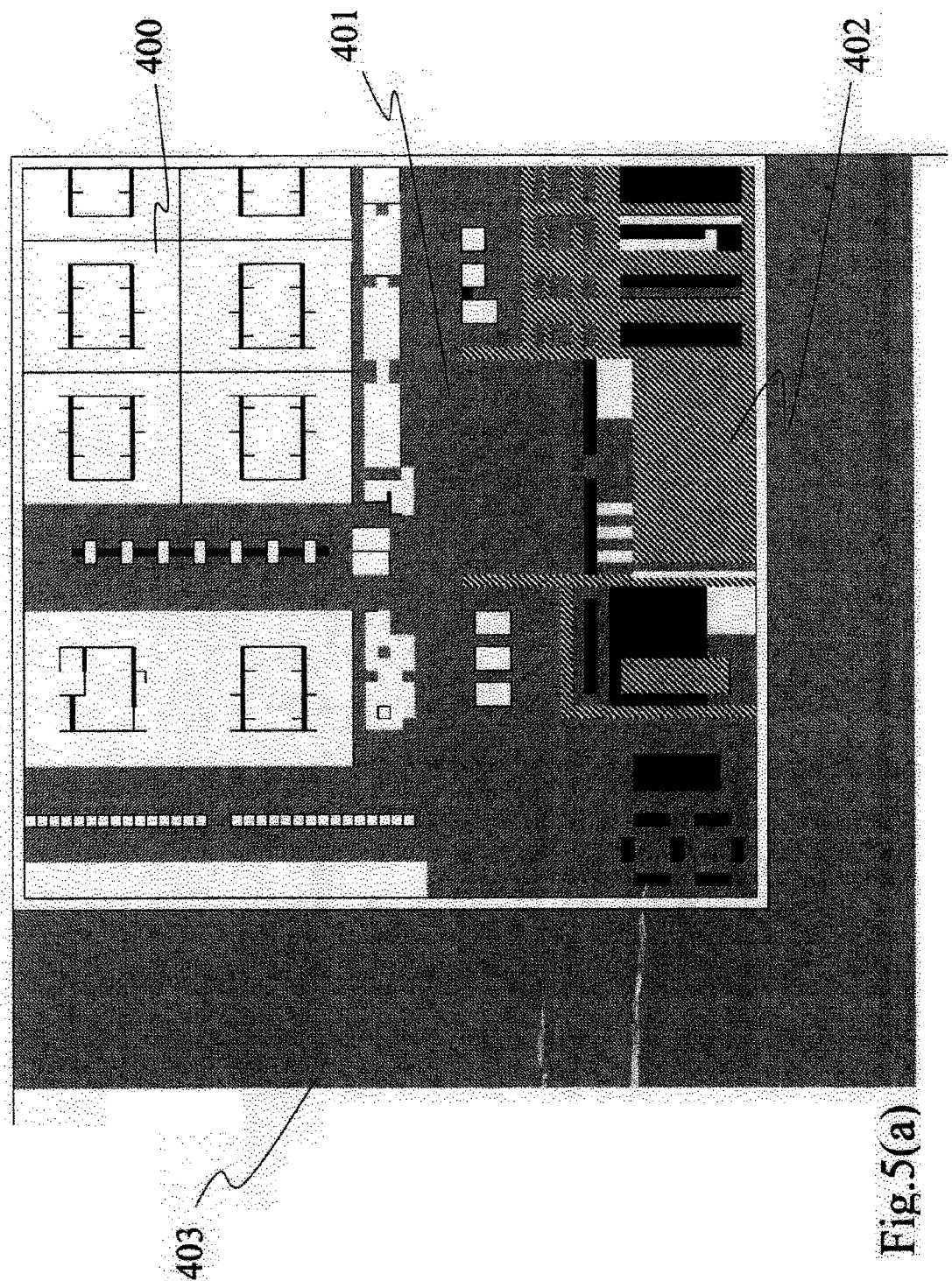
FIG. 5A shows an exemplary template used for image recognition in which each layer is provided with luminance information, FIG. 5B showing its corresponding OM image.
Figure 5B:
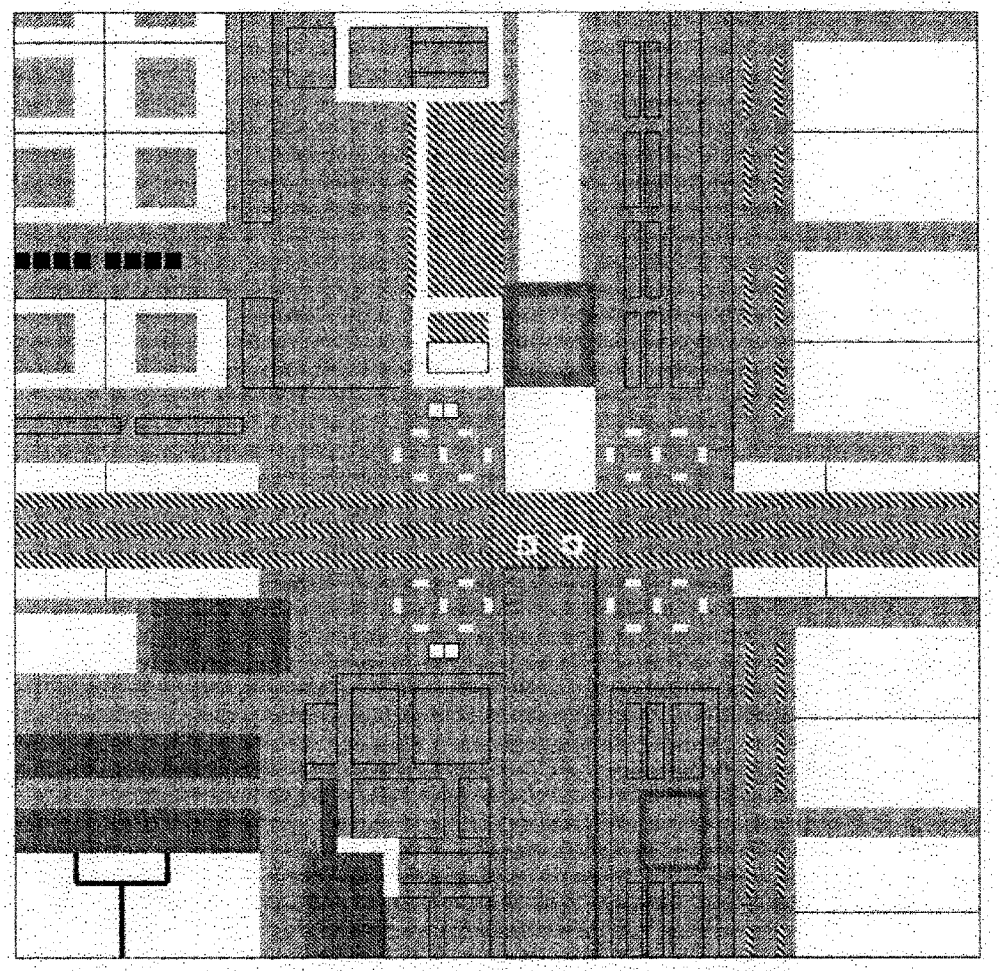
Figure 6A:
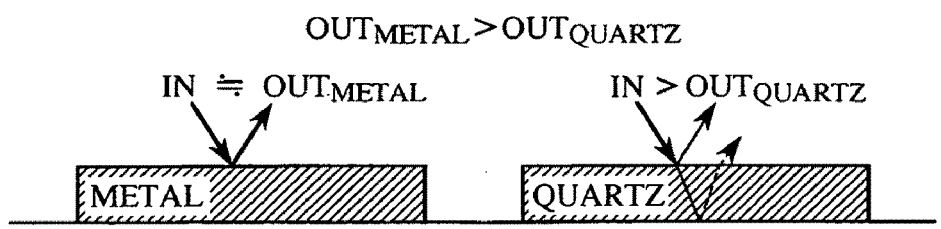
FIGS. 6A to 6D show the light reflection properties of various patterns.
Figure 6B:
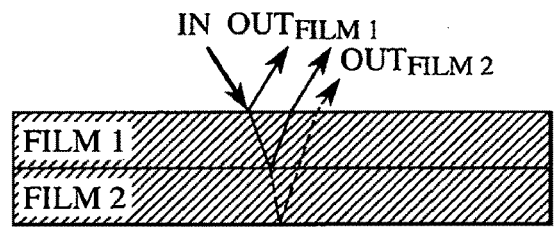
Figure 6C:
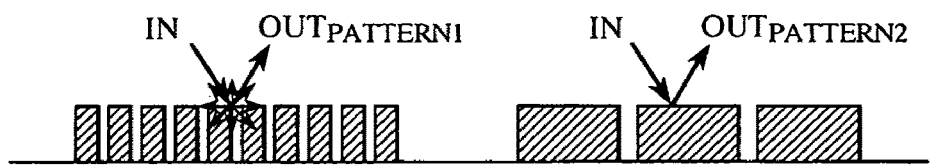
Figure 6D:
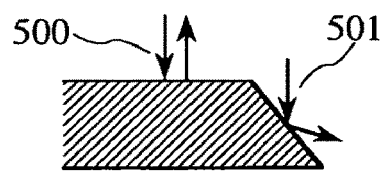

To solve this problem, different luminance levels (also called gradation levels or gray levels) are set for different design data layers, as shown in FIG. 5A. In the figure, an uppermost layer 400 of a sample has a high luminance level, a dummy layer 401 an intermediate luminance level, a lower layer 402 a low luminance level. Further, a background 403 has an intermediate luminance level. By thus setting an appropriate gray level for each layer, the information amount necessary for image recognition can be optimized. In addition, gray levels are also determined based on semiconductor element materials because their luminance levels are different when imaged.

The gray level setting is performed based on the following rules, as shown in FIG. 6. First of all, a metal layer and a quartz layer differ in reflectance, as shown in FIG. 6A: the reflectance of the metal layer is greater than that of the quartz layer. Thus, gray levels are set so as to reflect this relation. Further, as shown in FIG. 6B, the light reflection intensity of an upper layer is greater than that of a lower layer; thus, gray levels are also set so as to reflect this relation. Furthermore, as shown in FIG. 6C, a large pattern on a sample reflects the better part of incident light and thus has a higher light reflection intensity than a small pattern. Accordingly, gray levels are also set so as to reflect this relation, the light reflection intensity of a large pattern>the light reflection intensity of a small pattern. Moreover, the outlines of design data (sample patterns) are set black because they correspond to slanted portions of patterns as shown by a pattern edge 501 of FIG. 6D.

Applying gray colors to design data in this manner provides better information for image recognition, also improving the success rate of image recognition. In addition, the contrast information that had not been available with design data can also be utilized, thus increasing the diversity of applicable image recognition algorithms.

The above-mentioned gray level setting rules can also be combined in order to finalize a gray level. For example, a gray level can be determined by parameterizing 1) a pattern material, 2) the layer position where the pattern exist at the time of measurement, and 3) the pattern size and by taking these parameters collectively into consideration. Specifically, a gray level can be finalized by using such parameters as coefficients for the following formula, for example: gray level initial setup value×$A_n$ (coefficient defined according to material types)×$B_n$ (coefficient defined according to layers)×$C_n$ (coefficient defined according to pattern sizes), . . . , etc. In addition, the pattern size coefficient can be fixed (for example, to 1) if the sizes of patterns across a sample are uniform enough to be negligible. Moreover, the types of wafers or the like can also be parameterized to use them as coefficients.

The above gray level setting conditions are contained in design data of a semiconductor device. By examining the uppermost layer information at the time of sample measurement and image-acquisition positional information, gray levels can be derived with ease, and this process can also be put into an algorithm easily. In addition, instead of calculating gray levels each time the necessity arises, the relationships between the above parameters and gray levels can be put into a table in advance so that gray levels can be assigned easily without such calculation.

Figure 9:
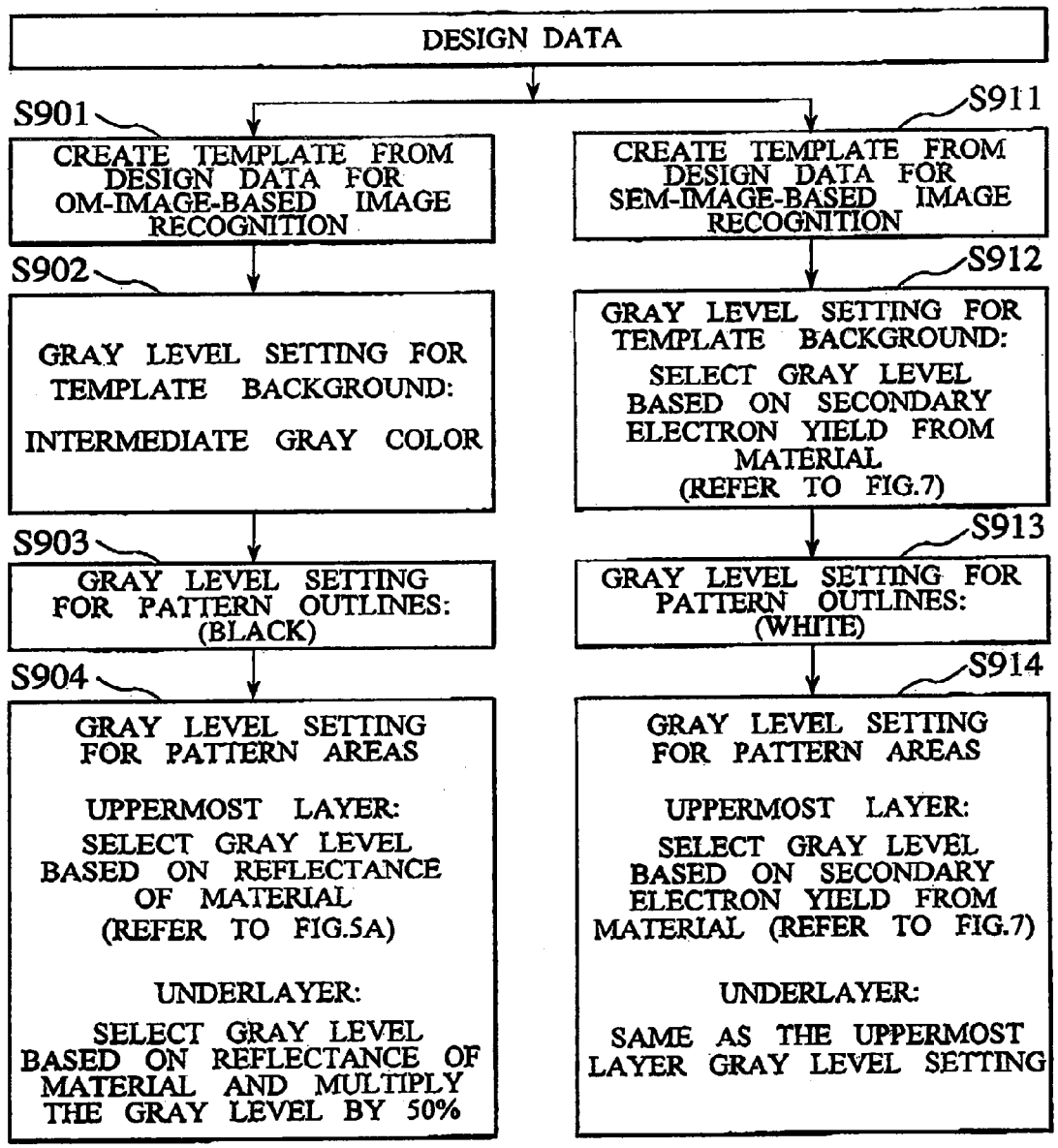
FIG. 9 is a flow chart showing the process of creating a template used for image recognition.

FIG. 9 is a flowchart illustrating the process flow of obtaining, based on design data, gray levels for a template image that is used for OM image recognition. First, in S901, a sample region to be registered as a template is selected from among the design data. In S902, a predetermined gray level is set for the background region in the selected sample region. The background gray level can be set as desired, but should preferably set at an intermediate gray level, which is neither too bright nor too dark. Next in S903, a low gray level (equivalent to zero gradation value; almost black) is set for the outlines (boundaries) of the patterns in the selected sample region. Finally in S904, gray levels are set for the pattern areas surrounded by the outlines in accordance with the above-mentioned gray level setting rules.

By following the above gray-level setting process to set gray levels for a template, an image recognition template close to an actual image can be created.

Described next is a gray level setting method for a template that is used for SEM image recognition. In contrast to OM images, SEM images vary in their luminance level depending on the efficiency in detecting secondary electrons or back-scattered electrons. Thus, gray levels are determined based on this electron detection efficiency.

The yield of secondary electrons from a sample is determined by 1) the landing energy of an incident electron beam (acceleration voltage with which the electron beam reaches the sample), 2) sample material, and 3) pattern edges on the sample. In addition, because a probe current for the electron beam also contributes in brightening SEM images, this current is also considered, when necessary, in determining gray levels. Further, when the acceleration voltage for the electron beam is high, this electron beam often reaches an underlayer region of the sample; in other words, when the acceleration voltage is greater than a predetermined value, underlayer patterns of the sample become visible that would otherwise be invisible with a low acceleration voltage. Thus, this can also be considered, if necessary, upon gray level determination.

Figure 8:
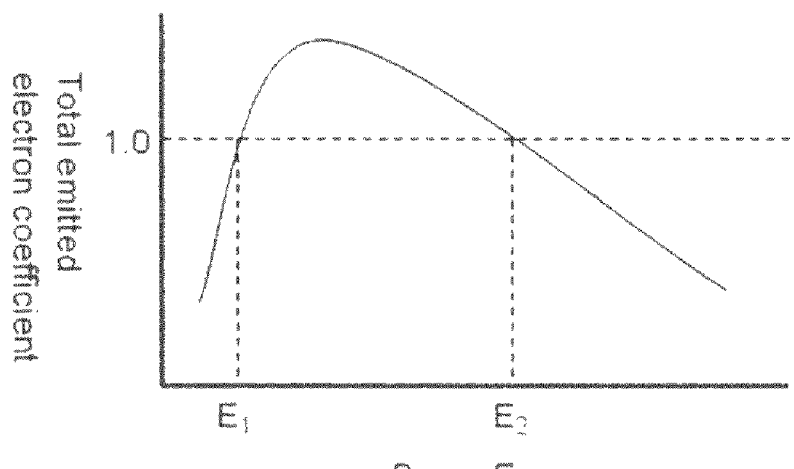
FIGS. 8A to 8C show the yield of secondary electrons that varies depending on material types and the setup conditions of the scanning electron microscope.
Figure 8:
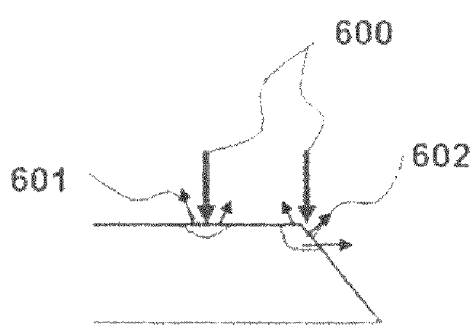

FIG. 8A is a graph illustrating the relationship between the landing energy of an incident electron beam onto a sample and the yield of secondary electrons from the sample. As can be seen in the figure, the yield of secondary electrons varies significantly according to the energy magnitude of the electron beam onto the sample. In other words, the sample luminance significantly changes according to the beam energy. For the purpose of setting appropriate gray levels according to the level of this sample luminance, the landing energy of electron beams is thus taken into consideration. The landing energy (LE) of an electron beam onto a sample takes the same value as the voltage (Vacc) that is applied to acceleration electrodes provided in an electron microscope. In SEMs that control the landing energy by applying a negative voltage (Vr) to a sample, the landing energy is obtained by subtracting the negative voltage from the acceleration voltage (LE=Vacc−Vr).

FIG. 8B is a table illustrating the relationship between sample types and the yield of secondary electrons. With that table, gray levels are set according to sample types. Further, as shown in FIG. 8C, secondary electrons are generated more from the edge portions of a pattern, and the edge portions thus tend to become brighter than the rest portions. Therefore, gray levels are preferably set such that the edge portions are made still brighter. Note that all of the above conditions need not be used: gray levels can be set using at least one of the conditions.

Explained next with reference to FIG. 7 are a gray-level-adjusted template and a template that is created based solely on design data. FIG. 7A is typical design data, and FIG. 7B is a template that is created based on the design data. FIG. 7C is part of an SEM image that is to be recognized with the template of FIG. 7B. FIG. 7D is a template obtained by adjusting the gray levels of the template of FIG. 7B. obviously, the gray-level-adjusted template of FIG. 7D is closer to the SEM image of FIG. 7C than the template of FIG. 7B that is created based solely on the design data.

Figure 7A:
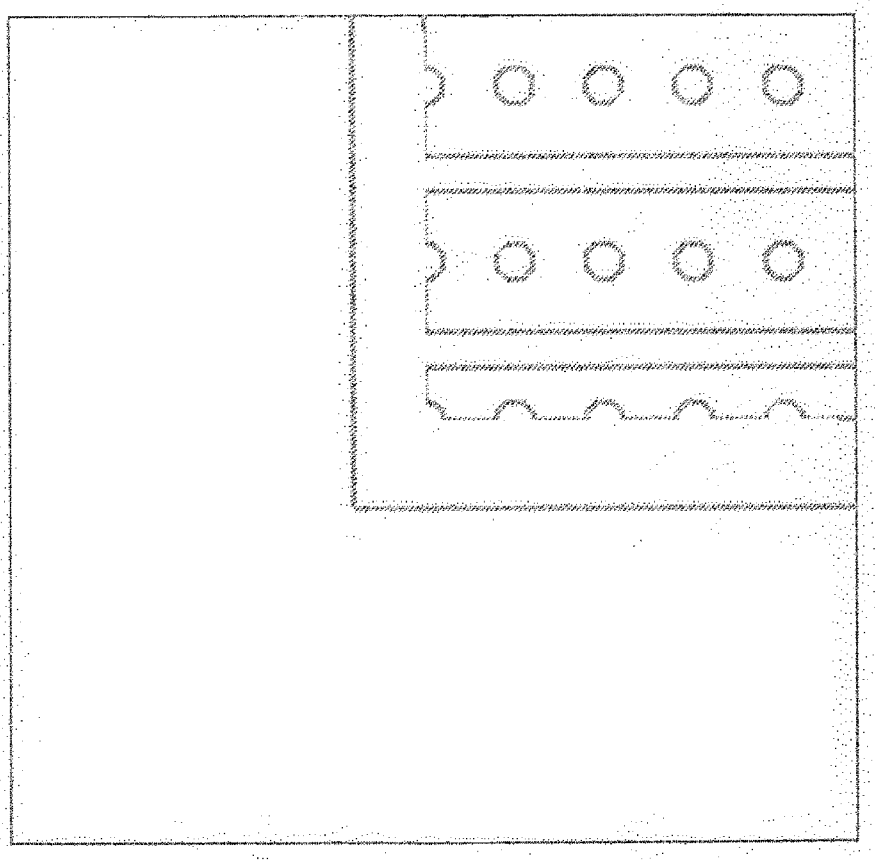
FIGS. 7A to 7D show an example of a gray-level-adjusted template used for image recognition.
Figure 7B:
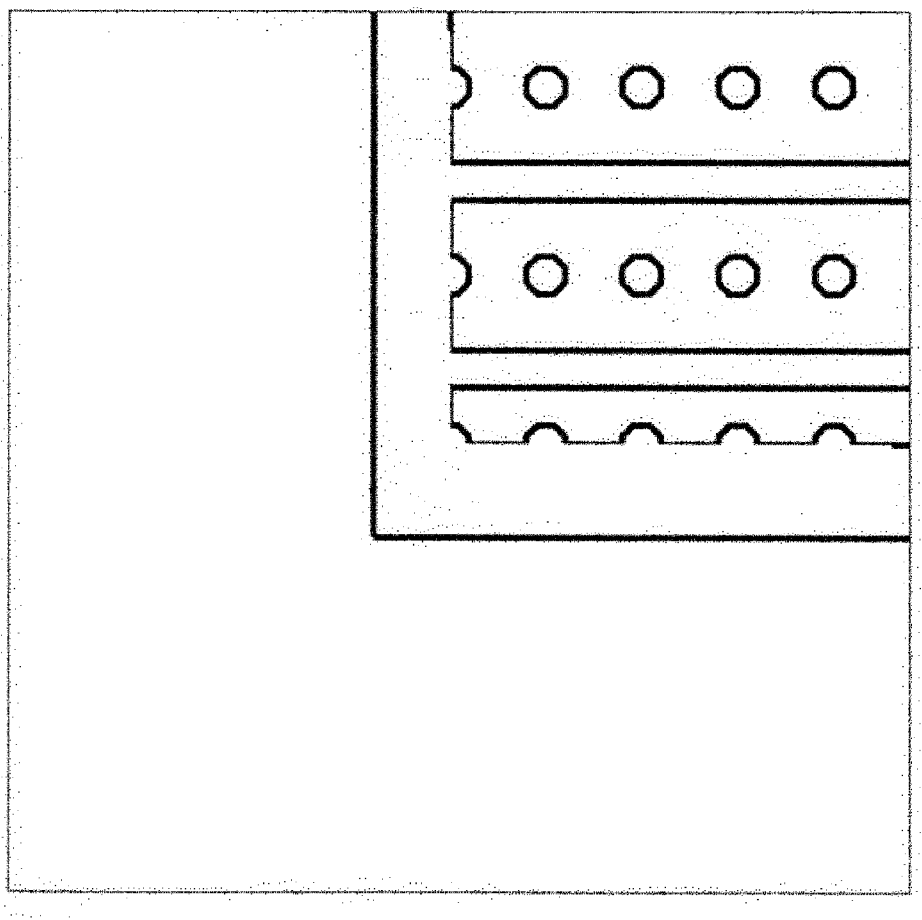
Figure 7C:
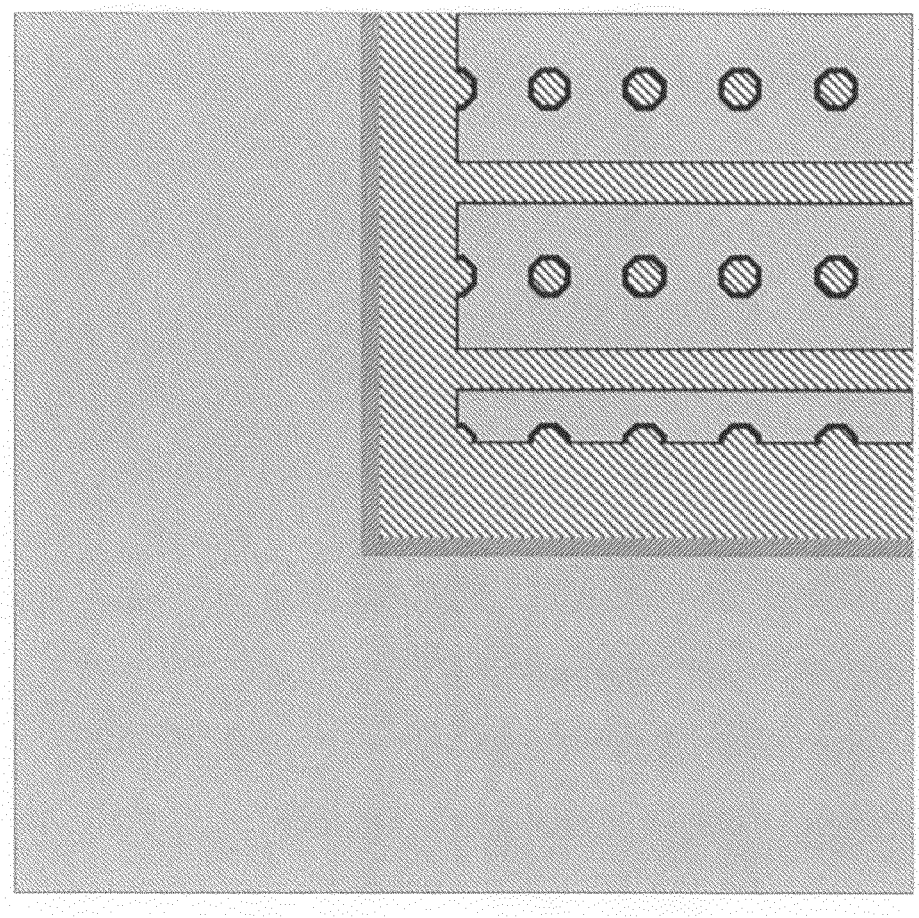
Figure 7D:
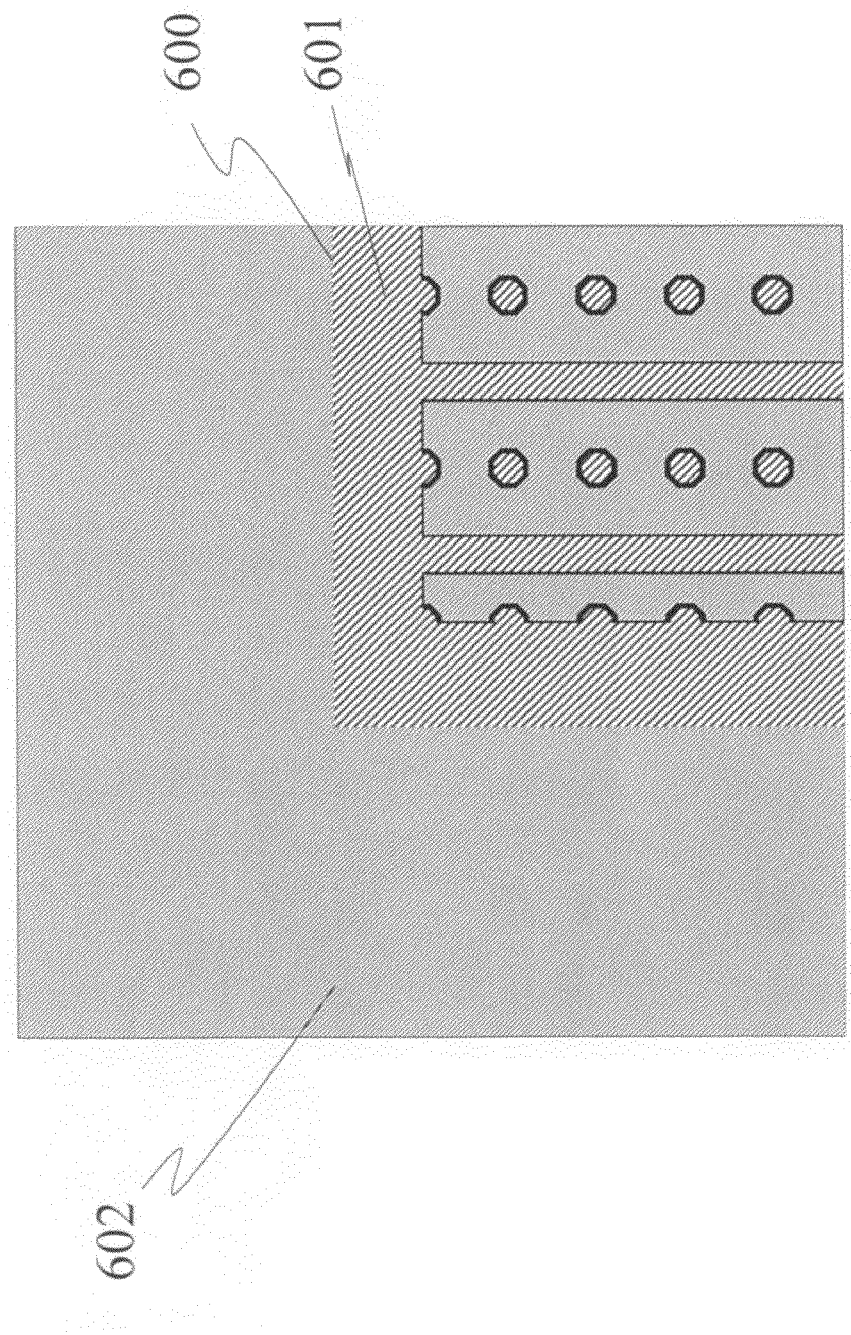

In the gray-level-adjusted template of FIG. 7D, an outline 600 corresponds to an edge portion where secondary electrons are generated more. Thus, the gray level for that portion is set high (in this example, the highest gradation level; almost white). Portions 601 and 602 are different in their material; thus, their gray levels are set according to material types pre-registered.

Steps S911 to S914 in FIG. 9 is a flowchart illustrating the process flow of obtaining, in accordance with the gray level setting conditions explained with FIGS. 8A to 8C, gray levels for a template image that is used for SEM image recognition. First, in S911, a sample region to be registered as a template is selected from among design data. In S912, a predetermined gray level is set for the background region in the selected sample region. The background gray level is set according to the yield of secondary electrons. Next in S913, a high gray level (white) is set for the outlines (boundaries) of the patterns in the selected sample region. As mentioned above, the outlines (boundaries) of a pattern correspond to the edge portions of that pattern on an actual device in which portions the yield of secondary electrons is high. Thus, a relatively high gray level is set in comparison with the rest portions. Finally in S914, gray levels are set for the pattern areas surrounded by the outlines in accordance with the yield of secondary electrons and material types. In this gray level setting for a template used for SEM image recognition, such parameters as mentioned earlier can also be used as coefficients and put into a table. In accordance with such rules as mentioned above, gray levels are set for each pixel or for each region defined by pattern outlines.

In accordance with the above configuration, a template image close to an actual image can be created based on the design data of a semiconductor device or on the setup conditions of microscopes without acquiring an OM image or SEM image. Further, when design data to which gray level information is added is subjected to differential processing, image recognition can be performed based on pattern edge information.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:
1. A method for creating based on design data a template that is used for image recognition by an imaging apparatus, wherein:
   the imaging apparatus is an optical microscope; and
   luminance information is set for each area in the template based on a combination of material information of the region defined by the template, pattern size information of a pattern arranged in the region defined by the template, and layer information of the region defined by the template.

2. A method for creating based on design data a template that is used for image recognition by an imaging apparatus, wherein:
the imaging apparatus is a scanning electron microscope; and
luminance information is set for each area in the template based on material information of the region defined by the template, setup conditions of the scanning electron microscope, and pattern outline information of a pattern arranged in the region defined by the template.

3. An image processing apparatus comprising:
an imaging apparatus forming an image using an optical microscope; and
a template creation unit for creating a template based on design data,
wherein the template creation unit creates the template based on luminance information set for each area in the template based on a combination of material information of the region defined by the template, pattern size information of a pattern arranged in the region defined the template, and layer information of the region defined the template.

4. An image processing apparatus comprising:
an imaging apparatus forming an image using a scanning electron microscope; and
a template creation unit for creating a template based on design data,
wherein the template creation unit creates the template based on luminance information set for each area in the template based on material information of the region defined by the template, setup condition of the scanning electron microscope, and pattern outline information of a pattern arranged in the region defined by the template.

* * * * *